United States Patent [19]

King et al.

[11] 4,063,821

[45] Dec. 20, 1977

[54] GAS DETECTOR TUBE READER

[75] Inventors: Charles A. King, Vienna; George E. Dyche, Centreville, both of Va.

[73] Assignee: General Kinetics, Incorporated, Rockville, Md.

[21] Appl. No.: 706,568

[22] Filed: July 19, 1976

[51] Int. Cl.² .............................................. G01B 11/02
[52] U.S. Cl. ..................................... 356/167; 356/201
[58] Field of Search ................ 356/201, 202, 203, 204, 356/205, 156, 167; 73/23

[56] References Cited

U.S. PATENT DOCUMENTS

| | | | |
|---|---|---|---|
| 3,246,334 | 4/1966 | Devereaux | 356/203 |
| 3,375,751 | 4/1968 | Engborg et al. | 356/202 |
| 3,518,013 | 6/1970 | Sanford et al. | 356/203 |
| 3,864,036 | 2/1975 | VanHeerentals | 250/559 |
| 3,917,413 | 11/1975 | Gorman et al. | 356/197 |

*Primary Examiner*—John K. Corbin
*Assistant Examiner*—R. A. Rosenberger
*Attorney, Agent, or Firm*—Cushman, Darby & Cushman

[57] ABSTRACT

The reader apparatus includes a clamp colocated with a photoelectric cell and lamp. A scale, e.g. calibrated in millimeters extends laterally from the photoelectric cell/lamp axis. A gas detector tube whose column of test particles is stained from one stain-starting end to a region part way therealong is clamped in the reader with its starting end of stain juxtaposed with the scale. The tube is manually moved axially until a portion of the lightest-in-color region is directly between the photoelectric cell and lamp. The transmitted light indicator is adjusted to align with one extreme on its scale. Then the tube is manually moved axially until a portion of the darkest-in-color region is directly between the photoelectric cell and lamp. The transmitted light indicator is adjusted to align with the other extreme on its scale. Finally the tube is slid axially until the indicator coincides with a preselected intermediate tick-mark, e.g. indicating a light transmittance value half-way between the two extremes. With the tube clamped at that location, the length of stain is read from the scale, by noting the site of juxtaposition of the starting end of stain on the scale. Accordingly, the more pronounced reading is made by the human and the measure that is harder for a human to make consistently is uniformly made by the device.

A particular clamp construction is disclosed, wherein fiber optics lead light from the lamp through one clamp jaw directly to the gas detector tube and from a diametrically opposed site on the tube through the other clamp jaw to the photoelectric cell.

13 Claims, 6 Drawing Figures

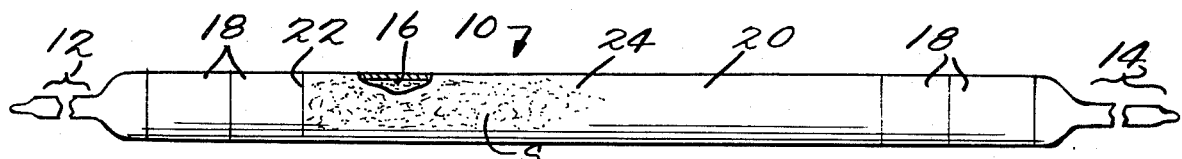
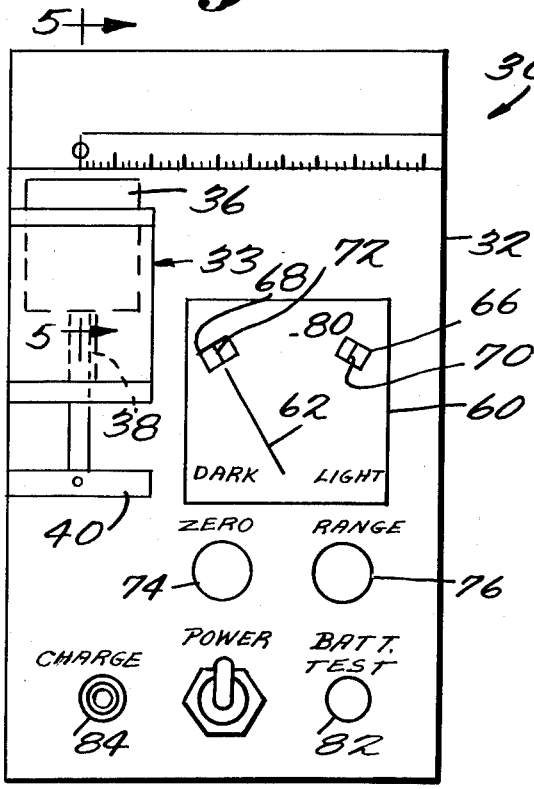
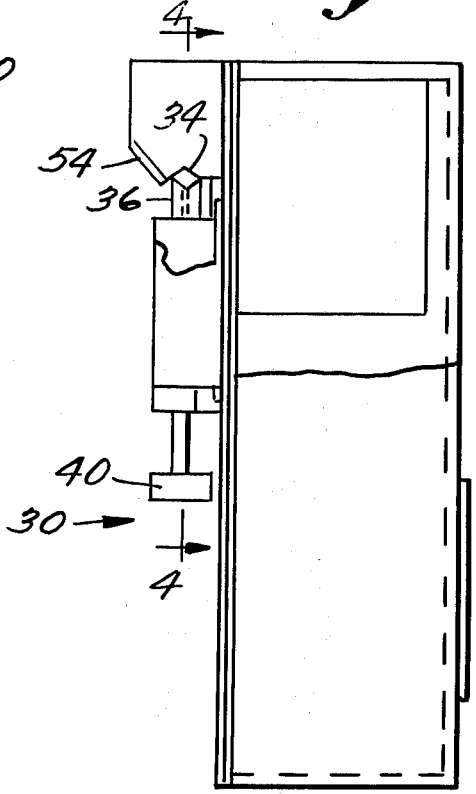
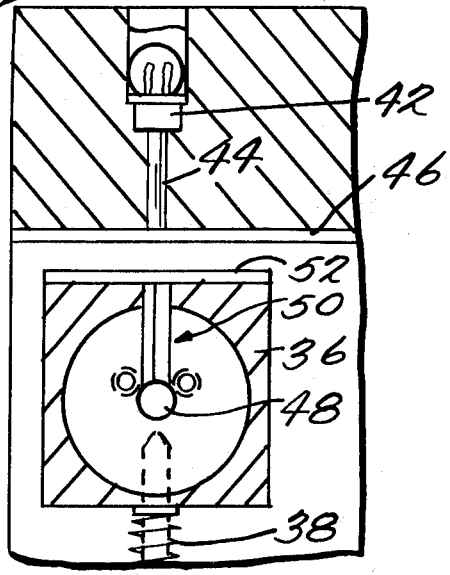
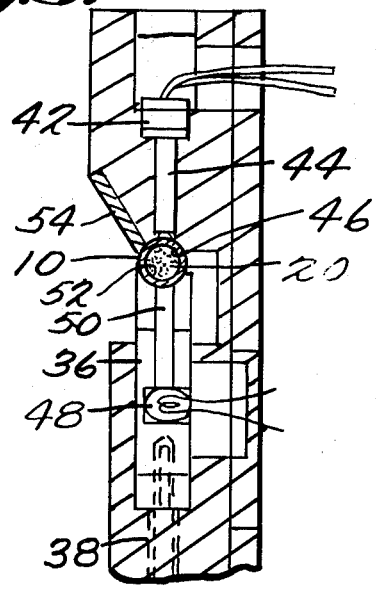

GAS DETECTOR TUBE READER

BACKGROUND OF THE INVENTION

The gas detector tubes of interest at present generally consist of small-diameter glass tubes containing at least one gas-permeable substrate impregnated with a chemical reagent which will change color when exposed to at least a minimum quantity of one or more specific gases. The gas detector tubes normally are prepared in advance by the manufacturer and sealed at both ends. In use, both ends of the tube are broken off and the tube is attached to the suction side of a calibrated air pump capable of drawing a predetermined volume of air (or air-gas mixture) through the substrate and reagent. When there is a sufficient concentration of the looked-for gas present in the air drawn through the tube, the specific reagent carried by the substrate begins to discolor at the upstream boundary (starting end) of the substrate packing and continues to discolor further down the length of the tube with increasing volume of flow. If the suction pump employed is properly calibrated and properly used, the input air flow usually is discontinued before all of the reagent in the tube becomes discolored. In most applications, the length of stain produced by reaction between the looked-for gas and the tube contents becomes an approximate measure of the specific gas concentration in the air sample drawn through the tube. Depending upon the apparatus manufacturer, various methods and aids are provided to the observer to assist in measuring the length of stain in the sampling tube. Such aids may consist of calibrated marks on the surface of the glass tube, measuring scales into which the tube can be inserted or nomograph charts along which the tube can be rolled to match the length of stain to the volume of air sampled and the appropriate date of manufacture and calibration for the particular batch of tubes employed.

Since gas detector tubes of the above type and their associated pump and measuring apparatus are relatively inexpensive, their use for environmental safety and health analyses can become widespread in sampling for various undesirable gases and vapors in concentrations at or near their Threshold Limit Values.

Until now, the lack of standardization of the manner in which individual people visually judge the exact location of the end-of-stain in obtaining detector tube readings has restricted the usage of these valuable indicators. While some stain demarcations are relatively sharp, all stain endings actually consist of a gradient of gradually decreasing stain with the exact end-point often very poorly defined. Under such conditions, it is not unreasonable to expect a substantial degree of scatter in readings made by individuals in a group of human observers. Visual measurements, where judgment is required, are subject to variations in lighting, visual acuity of observer and the states of stress, fatigue, and motivation of the observer. When one adds to this the normal variations and tolerances to be expected in manufacture of the sampling tubes, it is not surprising that at least one manufacturer publishes predicted relative standard deviations (for gas detector tubes of the same batch) ranging from 15% to 25%.

Important factors other than those discussed above may tend to compound the generation of discrepancies in length of stain readings made by different people at different places. One obvious problem is the phenomenon of fading of the stain after a comparatively short period of time. For instance, in attempting to measure concentrations of chlorine or nitrogen dioxide with some gas detector tubes, significant fading of the stain can be expected within a period of as little as 15 minutes. Conversely, in using one gas detector tube to test for sulphur dioxide it is necessary to wait for 10 minutes or more for the stain to develop fully before making the reading.

Somewhat more than 100 varieties of gas detector tubes presently are commercially available in the United States for detecting and measuring concentrations of gases and vapors in the Threshold Limit Value concentration ranges. While most of the stain reactions proceed from light to dark, the inverse is the case in a substantial number. The variety of colors that must be recognized occupies virtually the entire visible spectrum. In a few instances the length of the stain is less important as a concentration measure than the intensity or change of intensity of the stain relative to a standard color reference supplied with the particular detector tube concerned. In addition to the simple, single-packing tube, gas detector tubes also are employed which contain a pre-conditioning filter layer designed to remove interfering gases before the sample enters the final stain-reagent area of the tube. In another, more complex, form of gas detector tube a breakable reagent ampule is built into the tube. In such tubes the ampule is crushed by the operator to add a liquid or gaseous conditioning reagent to the sample air stream to activate the actual measurements.

SUMMARY OF THE INVENTION

The invention provides a reliable and inexpensive, compact and portable means for uniformly measuring the length of stain of gas detector tubes.

The reader apparatus includes a clamp colocated with a photoelectric cell and lamp. A scale, e.g. calibrated in millimeters extends laterally from the photoelectric cell/lamp axis. A gas detector tube whose column of test particles is stained from one end to a region part way therealong is clamped in the reader with its starting end of stain juxtaposed with the scale. The tube is manually moved axially until a portion of the lightest-in-color region is directly between the photoelectric cell and lamp. The transmitted light indicator is adjusted to align with one extreme on its scale. Then the tube is manually moved axially until a portion of the darkest-in-color region is directly between the photoelectric cell and lamp. The transmitted light indicator is adjusted to align with the other extreme on its scale. Finally the tube is slid axially until the indicator coincides with a preselected intermediate tick-mark, e.g. indicating a light transmittance value half-way between the two extremes. With the tube clamped at that location, the length of stain is read from the scale, by noting the site of juxtaposition of the starting end of stain on the scale. Accordingly, the more pronounced reading is made by the human and the measure that is harder for a human to make consistently is uniformly made by the device.

A particular clamp construction is disclosed, wherein fiber optics lead light from the lamp through one clamp jaw directly to the gas detector tube and from a diametrically opposed site on the tube through the other clamp jaw to the photoelectric cell.

The principles of the invention will be further discussed with reference to the drawings wherein a preferred embodiment is shown. The specifics illustrated in the drawings are intended to exemplify, rather than limit, aspects of the invention as defined in the claims.

BRIEF DESCRIPTION OF THE DRAWINGS
IN THE DRAWINGS

FIG. 1 is a side elevation view of a typical gas detector tube after its ends have been broken off and a preselected, standard volume of gas has been drawn therethrough causing the staining of an indicator column to progress part way along the column from one end thereof, as at least an approximate indication of the abundance of a particular chemical in the gas.

FIG. 2 is a front elevation view of a gas detector tube reader provided in accordance with the principles of the present invention;

FIG. 3 is a right side elevation view thereof;

FIG. 4 is a larger scale fragmentary sectional view taken substantially on line 4—4 of FIG. 3;

FIG. 5 is a fragmentary sectional view on the same scale of FIG. 4, taken on line 5—5 of FIG. 2.

DETAILED DESCRIPTION OF THE PRESENTLY PREFERRED EMBODIMENT

Figure 6:
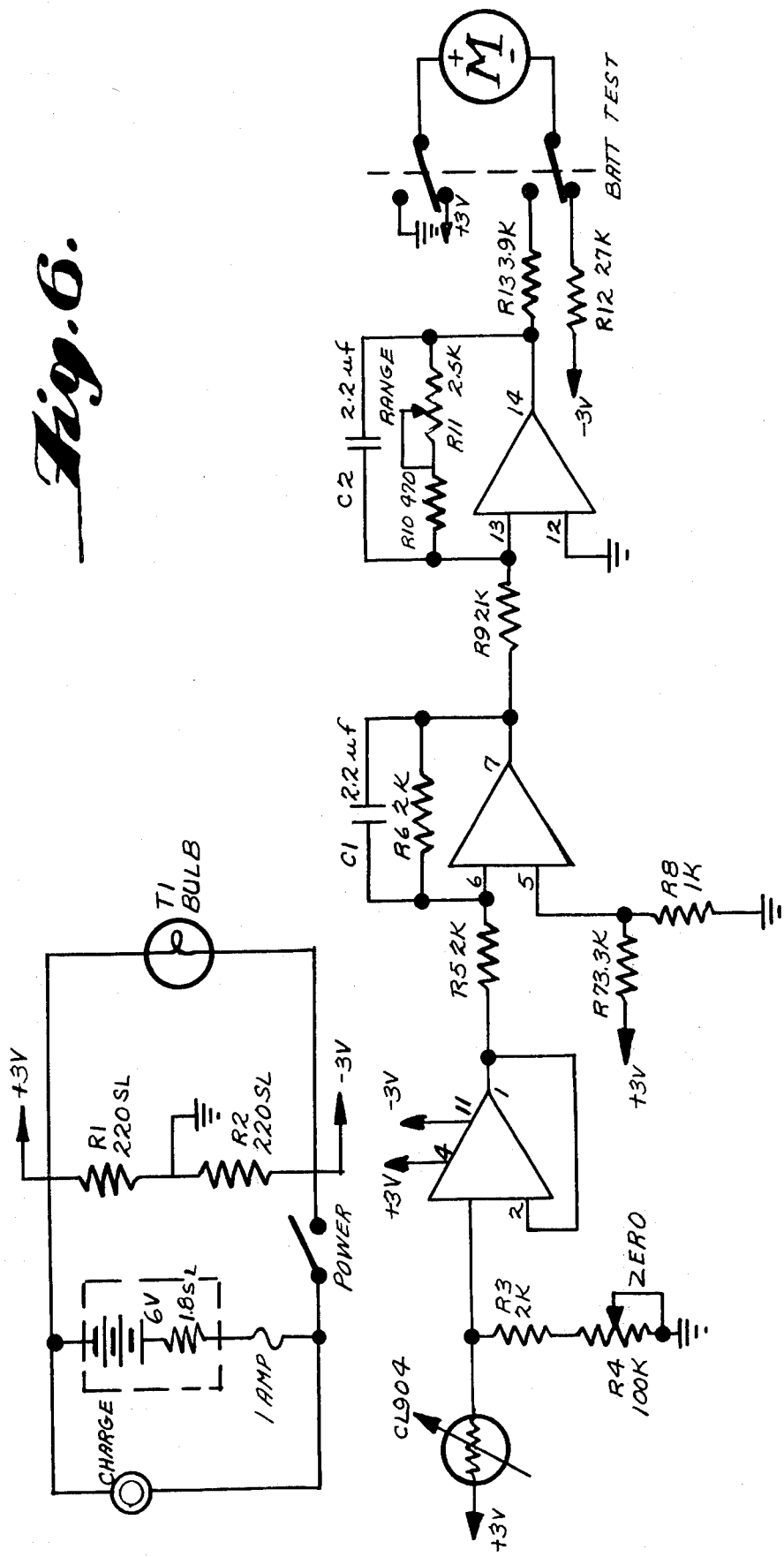
FIG. 6 is a typical schematic wiring diagram for the device of FIGS. 2-5.

The typical gas detector tube 10 is an elongated tubular glass ampule initially integrally sealed at both ends 12, 14. The bore 16 of the tube is a miniature packed column, generally about 4.0 mm. diameter and up to about 150 mm. long. The column packing typically includes at least one gas-porous plug means 18, of open cellular solid, woven or non-woven tangled filamentary and/or particulate inert material near each end and a uniform length column of indicator-bearing gas-porous material 20 such as silica gel kept in place by and between the plug means 18.

In use, the tips 12, 14 are first broken off, opening the bore 16 at both ends. Using a commercially available pump, not shown, a standard volume e.g. 1 liter of the gas to be sampled is drawn through the tube 10.

For the moment, assume that the gas being sampled is air possibly containing contaminant X, that the indicator-bearing material appears to be white in color, unless it is contacted by contaminant X, in which case the material which has been exposed turns brown. Of course, if the relative abundance of contaminant X is small, an insufficient amount will be drawn into the tube to discolor all the indicator-bearing material 20. In such a case, the end 22 of the column of indicator-bearing material nearest the open end of the bore 16 which served as the inlet as the gas sample was drawn through the tube will stain first, providing one, distinct end of stain. The staining will progress along the column of indicator-bearing material until no more contaminant X is left to react with the indicator, whereupon the pattern of staining S peters out as at 24. Whereas the end 22 is usually a plane substantially transverse to the tube and thus easy to locate visually with a high degree of certainty, the staining front at 24 is often indistinct, diffuse, distorted by idiosyncrasies of flow pathways through the column and irregular in shape.

If two people are asked to visually check and then mark the extent to which the stain front had progressed along the tube, generally their answers will not coincide because of the uncertainties just mentioned. A similar disparity can be expected when the same person is asked to mark the stain front in two succeeding trials.

The present invention provides a device 30 FIGS. 2-5 and a method by which the human user visually locates the distinct mark at 22, the device 30 is used to fix the site of the stain front at 24, whereupon the length of stain, between 22 and 24 can be routinely measured with a substantially greater degree of certainty than heretofore practical.

The reader device 30 includes a housing 32 which mounts a clamp 33 for removably holding the gas detector tube under examination. The clamp has a fixed jaw 34 and a movable jaw 36 that is spring-loaded at 38 to be urged toward the fixed jaw 34. The movable jaw includes a handle 40 which may be grasped and pulled down to temporarily separate the jaws. The fixed jaw is shown incorporating a photoelectric cell 42. A fiber optics rod means 4 that extends within the fixed jaw from the photoelectric cell to the concave face 46 of the fixed jaw 34. The movable jaw is shown incorporating an illuminating electric lamp 48 and a fiber optics rod means 50 that extends within the movable jaw from the lamp 48 to the concave face 52 of the movable jaw 36.

The jaw concave faces 46, 52 confront one another like parentheses and are curved or bent about a horizontal axis that extends widthwise of the front of the housing 32.

By preference, the fiber optics rod means 50 which illuminate the tube 10 is broader than the fiber optics means 44 which picks up light transmitted through the tube 10 and transmits it to the photoelectric cell. In the instance depicted, the fiber optics rod means 50 is constituted by two rods positioned parallel to one another and side-by-side, and the rod means 44 is constituted by one such rod, in axial alignment with the sum of the two rods of the fiber optics rod means 50. This provides more even illumination of the tube portion under examination and restricts the gathering of transmitted light to the center of the illuminated region.

A scale 54, preferably ruled in millimeters is preferably provided horizontally on the front of the housing 32, with its origin coinciding with the axis of the fiber optics rod means 44. Accordingly, when a tube 10 is held in the clamp 33 with its distinct end of stain 22 extended to the right upon the scale. The distance longitudinally of the tube between the tube portion under examination and the distinct end of stain 22 may be read directly from the scale.

The reader device 30 is typically used as follows. A tube 10 which has had both tips broken off and which had been exposed to a gas sample that contained sufficient contaminant to produce a stain extending from the distinct end 22 to a usually less distinct stain front at 24 is inserted in the clamp 33 by pulling down the handle 40, placing the tube, horizontally parallel to the housing front, between the two clamp jaws, and releasing the handle 40. The tube is slid back and forth until the lightest-in-color region of the indicator-bearing material is directly between the lamp's fiber optics rod means 50 and the photoelectric cell's fiber optics rod means 44. This does not call for a subjective judgment, but rather the user merely longitudinally slides the tube and watches the meter-dial 60. The meter's needle 62 swings to the right in direct proportion to increasing transmittance of light sensed by the photoelectric cell.

(The meter dial 60 has one two-color block 66 near the right-most extreme of the needle's swing and another two-color block 68 near the left-most extreme of the needle's swing. For example, the block 66 has a black right half and a green left half with a line 70 defined between the halves and the block 68 has a black left half and a red right half with a line 72 defined between the halves. The purpose of the structures just described is to provide fixed end points, at 70, 72 for the needle's swing, that are angularly short of the meter's mechanical limit pins.)

The knob 74 marked "Zero" is then turned until the meter needle, which has swung to the right is aligned with the line 70 of the block 66.

Then the tube is longitudinally slid to bring an unmistakably dark portion of the column in between the two fiber optics rod means 44, 50 and the tube is slid back and forth until the meter's needle has swung as far as it is going to go to the left.

The knob 76 marked "Range" is then turned until the needle aligns with the line 72 of the block 68.

In fact, the instrument 30 has now been adapted to the particular tube 10 being studied. The darkest part of the tube column will swing the needle to its left end mark and the lightest part of the tube column will swing the needle to its right end mark.

For a standard, it has been arbitrarily decided to define the site of the stain front as the location where the light transmitted from the lamp to the photoelectric cell through the tube column is half its particular maximum and minimum. Accordingly, a tick mark 80 is provided on the meter's dial exactly half way along the path of the needle's swing between the lines 70 and 72. Of course, if another standard were selected, e.g. where the transmission is cut by one-fourth, one-third or the like could be adopted and tick marks correspondingly provided on the meter's dial.

Accordingly, the site of the stain front is located by next sliding the tube longitudinally with the region 24 being brought across the light path from the lamp to the photoelectric cell through the fiber optics, until the meter's needle exactly aligns with the tick mark 80.

Then the length of stain from the site of the stain front 24 to the end of stain 22 can be read in millimeters by noting where the distinct end of stain 22 lies on the scale.

If the clamp tightly grips the tube, longitudinal movement of the tube may require temporarily pulling down the movable jaw handle somewhat. Once the reading has been taken for a particular tube, it may be removed by pulling down the jaw handle and sliding it out. Another tube to be read may be slid in and the same set of steps followed. After brief practice, even the user with no special skills can easily read many tubes rapidly, one after another.

Note that by preference, the reader 30 further includes a conventional battery test circuit 82 and a conventional provision for charging the battery 84.

It should be apparent that in some instances, the lightest-in-color e.g. white part of the column will be the unstained region and the darkest-in-color e.g. green part will be the stained region. However, the reverse in true for other instances, e.g. wherein exposure to contaminant turns the exposed region from pink to blue or from brown to yellow or the like.

Note that the lamp and photoelectric cell are situated in the respective jaws as described as a matter of preference. Their relative locations could be exchanged.

In the past, some tubes 10 have been provided with scales stencilled or etched directly thereon. It is preferable to use unmarked tubes with the instrument 30, to avoid the necessity of being sure to rotate the tube until the markings are out of the light path. Generally, such scales would read backwards compared to the scale provided on the instrument housing, since it is customary in marked tubes, to have the scale origin coincide with the distinct end of stain 22.

While it is preferred that the scale for measuring length of stain be provided directly upon the instrument housing, with its origin coincident with the lamp/photoelectric cell axis, if a mark were placed on the housing to definitely locate that axis, a separate scale could be laid along the tube, with its origin on such work, for measuring the length of stain.

It should now be apparent that the gas detector tube reader as described hereinabove, possesses each of the attributes set forth in the specification under the heading "Summary of the Invention" hereinbefore. Because the gas detector tube reader can be modified to some extent without departing from the principles of the invention as they have been outlined and explained in this specification, the present invention should be understood as encompassing all such modifications as are within the spirit and scope of the following claims.

What is claimed is:

1. For reading the length of stain from a gas detector tube which tube includes a transparent, elongated tubular sidewall having an inlet end and an outlet end and having a filling of indicator-bearing, gas porous material which is specific to a looked-for constituent in the sense that said material turns color progressively along the tube when exposed to a gas including the constituent as a sample of the gas is drawn through the tube, so that a distinct end of stain is first produced at the end of said filling of indicator-bearing, gas porous material nearest the inlet end of the tube and until the constituent is exhausted a stain front progresses along said filling of the tube toward the outlet end of the tube, a gas detector tube reader, comprising:

a housing having:
 a. means for releasably clamping an individual gas detector tube and for permitting the tube while clamped to be moved longitudinally;
 b. an illuminated lamp and means for directing illumination thereof in a beam transversally upon an axial section of the tube while clamped;
 c. a photoelectric cell aligned with said beam transversally opposite the location of said illuminated axial section, and means for substantially confining the access of light to the photoelectric cell to such light of said beam as is transmitted generally transversally through the tube;
 d. a meter electrically connected to the photoelectric cell and constructed to provide an output proportional to the light reaching the photoelectric cell;
 e. first mark means on the housing coincident from the standpoint of an observer before the reader with the longitudinal axis of said beam;
 f. second mark means on the meter, intermediate the two extremes of meter output characteristic of most stained and least stained sections of the tube being read, whereby the length of stain of the gas detector tube being read may be measured as the distance along the tube length from said first mark means to the distinct end of stain, when the tube has been slid longitudinally until the meter output coincides with said second mark means.

2. The gas detector tube reader of claim 1, wherein: the means for releasably clamping a tube includes two opposed clamp jaws and means for moving one clamp jaw toward and away from the other, the two clamp jaws having tube-contacting surface means which confront one another;

the illumination directing means comprising first fiber optics rod means extending from the illuminated lamp, through one of said clamp jaws to said tube-contacting surface means of said one clamp jaw;

the light access confining means for said photoelectric cell comprising second fiber optics rod means extending from the photoelectric cell, through the other of said clamp jaws to said tube-contacting surface means of said other clamp jaw;

said first and second fiber optics rod means, where they emerge at the respective tube-contacting surface means being in axial alignment with one another.

3. The gas detector tube reader of claim 1, further including:

means defining a scale graduated in units of length, provided on the housing with the origin thereof at said first mark means and elongated in the same direction that a tube extends longitudinally when clamped by said releasable clamping means, whereby the length of stain may be read directly from the reader.

4. The gas detector tube reader of claim 1, wherein: said second mark means is disposed half way between said two extremes.

5. The gas detector tube reader of claim 1, wherein: the meter includes adjustment means for adjusting the meter output to one extreme thereof when the light reaching the photoelectric cell has actually been transmitted through the lightest-in-color section of said tube filling, and means for adjusting the meter output to the other extreme thereof when the light reaching the photoelectric cell has actually been transmitted through the darkest-in-color section of said tube filling.

6. Th gas detector tube reader of claim 5, wherein: the meter is a current flow sensing meter provided in an electrical circuit with the photoelectric cell; the meter having a swingable indicator needle viewable against a scale; said scale having a distinctive mark designating each of said two extremes and bearing said second mark means intermediate said distinctive marks.

7. The gas detector tube reader of claim 6, wherein: the distinctive marks designating the two extremes subtend at least a slightly smaller arc than that through which the indicator needle is swingable, so that when the meter is operated between said two extremes, the user can be sure the needle is not giving a false reading by being jammed against an end of the needle's arc of swingability.

8. For reading the length of stain from a gas detector tube which tube includes a transparent, elongated tubular sidewall having an inlet end and an outlet end and having a filling of indicator-bearing, gas porous material which is specific to a looked-for constituent in the sense that said material turns color progressively along the tube when exposed to a gas including the constituent, as a sample of the gas is drawn through the tube, so that a distinct end of stain is first produced at the end of said filling of indicator-bearing, gas porous material nearest the inlet end of the tube and until the constituent is exhausted a stain front progresses along said filling of the tube toward the outlet end of the tube, a method which comprises:

a. moving the tube along its own longitudinal axis with axially successive segments of the tube filling in the transversally crossing path of a lamp-to-photoelectric cell beam of light while noting both the maximum and the minimum output of the photoelectric cell, as indication of the light transmittance through unstained and fully stained portions of the tube filling;

b. maintaining the position of the tube relative to the beam when the photoelectric cell provides a preselected intermediate value of output, as an indication of the point along the length of the tube to which the stain front has progressed; then c. measuring the distance along said tube between the intersection of the beam and tube at said position and the distinct end of stain as an indication of the length of stain.

9. The method of claim 8, further comprising:

while conducting steps (a) and (b), displaying the photoelectric cell output on an electric current sensing meter which includes marks denoting the minimum, preselected intermediate and maximum outputs of the photoelectric cell output; and putting step (b) into effect when the sensing meter indicates the mark denoting said preselected intermediate output.

10. The method of claim 8, further comprising:

leading the beam along said path from the lamp to the tube in at least one fiber optics rod and from the tube to the photoelectric cell in at least another fiber optics rod.

11. The method of claim 8, wherein:

the maintaining step is carried out by releasably clamping the tube relative to the lamp and photocell.

12. The method of claim 8, wherein:

the preselected intermediate value of output is chosen as being midway between the maximum and minimum outputs of the photoelectric cell.

13. A method for uniformly measuring the distance along an elongated translucent two color element between a first imaginary transverse plane where the element definitely begins having one of the two colors, and a second imaginary transverse plane axially spaced along the element from the first, by which second plane, the element is substantially into transition between said one color and the other of said two colors, comprising:

a. moving the element along its own longitudinal axis relative to a beam of light that transversally crosses the element on a path between an illuminated lamp and a photoelectric cell including intersecting the element with the beam on both sides of the second plane, while noting both the maximum and minimum output of the photoelectric cell, as indications of light transmittance through regions of each of said two colors;

b. maintaining the position of the element relative to the beam when the photoelectric cell provides a preselected intermediate value of output, as an indication of intersection of the beam with said second plane; and c. measuring the length along the element between the intersection of the beam and element at said position and said first plane as an indication of said distance.

* * * * *